United States Patent [19]

Bakas et al.

[11] Patent Number: 4,777,312

[45] Date of Patent: Oct. 11, 1988

[54] PROCESS FOR THE ISOMERIZATION OF DIMETHYLNAPHTHALENES

[75] Inventors: Steve T. Bakas, Downers Grove; Paul T. Barger, Arlington Heights, both of Ill.

[73] Assignee: UOP Inc., Des Plaines, Ill.

[21] Appl. No.: 138,249

[22] Filed: Dec. 28, 1987

Related U.S. Application Data

[63] Continuation-in-part of Ser. No. 932,113, Nov. 18, 1986, Pat. No. 4,735,929, which is a continuation-in-part of Ser. No. 772,099, Sep. 3, 1985, abandoned.

[51] Int. Cl.$^4$ .................................................. C07C 5/22
[52] U.S. Cl. ...................................... 585/481; 585/482
[58] Field of Search ................................. 585/481, 482

[56] References Cited

U.S. PATENT DOCUMENTS 3,890,403 6/1975 Shimada et al. ............... 260/674 N

*Primary Examiner*—Curtis R. Davis
*Attorney, Agent, or Firm*—Thomas K. McBride; John F. Spears, Jr.; A. Blair Hughes

[57] ABSTRACT

Superior isomerization performance is obtained in an isomerization process employing a catalytic composition comprising a Group VIII noble metal and a hydrogen form mordenite incorporated with alumina. The superior isomerization performance is achieved using a catalyst composition having a surface area of at least 580 $m^2/g$. A novel method of preparing an isomerization catalyst having a surface area of at least 580 $m^2/g$ is characterized by contacting a formed catalytic composite with an acidic aqueous solution prior to addition of the Group VIII noble metal. The isomerization process is particularly useful in the isomerization of a dimethylnaphthalene containing feedstock into a product that contains a higher concentration of the 2,6-dimethylnaphthalene isomer than did the feedstock.

10 Claims, No Drawings

PROCESS FOR THE ISOMERIZATION OF DIMETHYLNAPHTHALENES

CROSS-REFERENCE TO RELATED APPLICATIONS

This application is a continuation-in-part of prior copending application Ser. No. 932,113 filed Nov. 18, 1986, which is a continuation-in-part of application Ser. No. 772,099 filed Sept. 3, 1985, now abandoned, the contents of which are incorporated herein by reference thereto.

BACKGROUND OF THE INVENTION

The present invention is related to a hydroisomerization process employing an improved catalytic composition. More particularly, this invention involves an isomerization process employing a catalyst composition comprising a hydrogenation function selected from the Group VIII metals, a hydrogen form crystalline aluminosilicate zeolite, and a refractory inorganic oxide.

The isomerization of alkylaromatics is well established in the art. This reaction is of considerable importance in the petroleum industry because of the substantially high value of certain alkylaromatics as starting materials in the production of polymers and polyester resins. Especially valuable is 2,6-dimethylnaphthalene (DMN) which is used in the production of polyesters. It has been the practice up until this time to isomerize alkylated aromatics to equilibrium mixtures of their isomers with a variety of catalysts. Friedel-Crafts catalysts, such as aluminum chloride, are known to be effective isomerization catalysts. Noble metals, such as platinum supported on halogenated alumina or silica alumina have also been used effectively to isomerize hydrocarbons. More recently, crystalline aluminosilicate zeolites which have shown catalytic activity have been effectively used in the isomerization of hydrocarbons. Both natural and synthetic crystalline aluminosilicates have been employed. Included among these are the Type X and Type Y zeolites as well as synthetic mordenite.

Specifically, the zeolites known as mordeniteshave received great attention. Mordenites are crystalline natural or synthetic zeolites of the aluminosilicate type: generally, they have a composition expressed in moles of oxide of

$1.0\pm0.2Na_2O.Al_2O_3.10\pm0.5SiO_2;$ the quantity of $SiO_2$ may also be larger. Instead of all or part of the sodium, other alkali metals and/or alkaline earth metals may be present.

In general, it is known that the sodium form of mordenite is not particularly effective for isomerization of hydrocarbons and that replacing all or, for the greater part, the sodium cations with hydrogen ions yields the more advantageous hydrogen form mordenite. Conversion of the sodium form to the hydrogen form can be accomplished by a number of means. One method is the direct replacement of sodium ions with hydrogen ions using an acidified aqueous solution where the process of ion exchange is employed. Another method involves substitution of the sodium ions with ammonium ions followed by decomposition of the ammonium form using a high temperature oxidative treatment.

The activity and selectivity of hydroisomerization catalysts depend on a variety of factors, such as the mode of catalyst preparation, the presence or absence of promoters, quality of raw materials, feedstock quality, process conditions, and the like. Suitable catalysts can be conventionally prepared by combining commercially available crystalline zeolites, such as, a hydrogen form mordenite, with a suitable matrix material followed by the addition of a Group VIII metal, and thereafter activating by conventional means. A new catalyst has been discovered which exhibits greatly improved isomerization performance when compared to conventionally prepared catalysts. It has been found to have particular use in a process to isomerize dimethylnaphthalene containing alkylaromatics preferably into 2,6-dimethylnaphthalenes.

OBJECTS AND EMBODIMENTS

Accordingly, there is provided a process for the isomerization of isomerizable hydrocarbons, which utilizes a feedstock containing dimethylnaphthalenes such that the concentration of the 2,6-dimethylnaphthalene isomer in the isomerization reaction product is greater than that of the hydrocarbon feedstock. The process comprises contacting the hydrocarbon feedstock with an isomerization catalyst in an isomerization reaction zone operating at isomerization reaction conditions and recovering the isomerization reaction zone products. The isomerization catalyst comprises a Group VIII metal, and a hydrogen form mordenite dispersed in an alumina matrix. The catalyst, comprised of from about 5 to 25 percent by weight of alumina and about 75 to 95 percent by weight mordenite is contacted with an acidic aqueous solution after it is formed and before the Group VIII metal component is incorporated into the catalyst. The contacting step occurs at conditions selected to increase the surface area of the composite to at least 580 m$^2$/g without increasing the silica to alumina ratio of the mordenite.

In a most preferred embodiment, the isomerization process of the present invention isomerizes a hydrocarbon feedstock containing at least 25 wt. % dimethylnaphthalenes such that the concentration of the 2,6-dimethylnaphthalene isomer in the isomerization reaction product is greater than the concentration of the 2,6-dimethylnaphthalene isomer in the hydrocarbon feedstock. The process comprises contacting the hydrocarbon feedstock with an isomerization catalyst in an isomerization reaction zone operating at isomerization reaction conditions. The isomerization reaction conditions include a temperature of from 300° to 450° C., a pressure of from about 1 to 20 atmosphere, a liquid hourly space velocity of from about 0.5 to 5 hr$^{-1}$, and a hydrogen to hydrocarbon molar feed ratio of from about 1 to 7. The final step is recovering the isomerization reaction zone products. The isomerization catalyst comprises from 0.1 to 2.0 wt. % platinum and a hydrogen form mordenite dispersed in a gamma-alumina matrix. The catalyst support comprises from about 5 to 25 wt. % gamma-alumina. After forming, the support is contacted with an acidic aqueous solution. The contacting occurs at conditions selected to increase the surface area of the composite to at least 580 m$^2$/g without increasing the silica to alumina ratio of the mordenite.

These, as well as other embodiments of the present invention, will become evident from the following, more detailed description.

INFORMATION DISCLOSURE

The prior art recognizes a myriad of catalyst formulations for the isomerization of hydrocarbons. It is well known that acids such as strong mineral acids can be used to modify crystalline aluminosilicate zeolite powders through decationization and dealumination. Ammonium compounds have also been successfully employed to convert crystalline aluminosilicates from alkali and/or alkaline metal cation form to the hydrogen form. Combinations of zeolites and refractory inorganic oxides have been disclosed, however, the art is silent as to the inherent problem of loss of the zeolite surface as a result of dilution and forming technique associated with the refractory inorganic oxides.

Combinations of the acid and ammonium treatments have been disclosed for use on aluminosilicate powders. U.S. Pat. No. 3,475,345 (Benesi) disclosed a method of converting aluminosilicate zeolites, particularly a sodium form synthetic mordenite, to the hydrogen form utilizing a three-step pretreatment performed on the powdered zeolite. These pretreatment steps consist of (1) a hot acid treatment, (2) a cold acid treatment, and (3) treatment with an ammonium compound. U.S. Pat. No. 3,442,794 (Van Helden et al.) also discloses a method for the pretreatment of aluminosilicate zeolites to the hydrogen form. Again, the preferred zeolite is the synthetic sodium form of mordenite. The method disclosed is very similar to U.S. Pat. No. 3,475,345 mentioned above, with the distinguishing feature being a separately performed two-step pretreatment with (1) an acid compound, and (2) an ammonium compound in arbitrary order. An important feature of both references is that the treatments are performed solely on the aluminosilicate zeolite with the express intention of modifying said zeolite before being utilized in a catalyst formulation. No mention of the importance of the surface area of the catalytic composite is disclosed in either reference. This is distinguished from the present invention in that any treatment performed is subsequent to the zeolite being incorporated into a formed catalyst composite and more importantly without any apparent modification of the zeolite itself.

Treatment of the aluminosilicates with acid have not only been effective for conversion to the hydrogen form, but also have been used as a means for increasing the silica to alumina ratio. Typically, a silica to alumina ratio of about 10:1 is observed for a sodium form synthetic mordenite and is substantially unchanged if an ammonium treatment is used to convert the mordenite to the hydrogen form. If a mordenite powder is subjected to an acid treatment as taught in U.S. Pat. No. 3,597,155 (Flanigen), an increase in the silica to alumina ratio is effected. The acid treatment is believed to cause a reduction of the framework tetrahedra aluminum atoms, thus increasing the proportion of silicon atoms present in the zeolitic structure. Isomerization performance is enhanced when the silica to alumina ratio of a mordenite powder is increased. As taught in U.S. Pat. No. 3,507,931 (Morris et al), a silica to alumina ratio above about 20:1 significantly improves the isomerization of light hydrocarbons. U.S. Pat. No. 4,018,711 (Bertolacini) also teaches that isomerization performance is improved if a pretreated mordenite powder having a silica to alumina ratio of at least 19:1 is incorporated in a catalytic composition. Again, these references specifically teach the use of acid treatment on the zeolite powder alone for the purpose of increasing the silica to alumina ratio, whereas the subject invention incorporates an already high silica to alumina ratio crystalline aluminosilicate into the catalytic composite. These references also do not teach the importance of the surface area of the catalytic composite or its relationship to isomerization performance.

Processes which employ isomerization steps to produce 2,6-dimethylnaphthalenes are known in the prior art. One in particular, U.S. Pat. No. 3,890,403 describes a combination process that employs an isomerization step to produce 2,6-dimethylnaphthalene. The isomerization step disclosed may employ a mordenite catalyst. However, the isomerization catalyst disclosed in U.S. Pat. No. 3,890,403 does not contain a Group VIII metal component, nor does it undergo an aqueous acidic solution washing step following base formulation.

A common attribute of most of the above mentioned prior art is that, in all cases, the crystalline aluminosilicate alone, in particular the synthetic sodium form of mordenite, is subjected to an acid and/or an ammonium pretreatment step(s) to modify the aluminosilicate before its incorporation into the catalyst composition. Although the pretreatment of mordenite as described in the above reference enhances the isomerization performance of catalytic composites comprising such pretreated mordenite, further improvements are still obtainable.

DETAILED DESCRIPTION

While previous work dealt exclusively with pretreatment of the aluminosilicate component of an isomerization catalyst, it is one of the objects of the present invention to provide a novel isomerization process utilizing a novel isomerization catalyst which is characterized by exceptionally high surface area and which exhibits improved isomerization performance. The isomerization process is characterized in that it isomerizes a feedstock containing dimethylnaphthalenes to produce a product which contains more of the 2,6-dimethylnaphthalene isomer than the feedstock contained.

According to the present invention, there is provided a process for the isomerization of a dimethylnaphthalene hydrocarbon into a produce richer in the 2,6-dimethylnaphthalene isomer than the feedstock. The catalyst composition useful in the present process comprises a Group VIII noble metal, hydrogen form mordenite, and from about 5 to 25 wt. % alumina with said catalyst composition having a surface area of at least 580 m$^2$/g. We have found that significant improvements in isomerization performance are realized when the surface area of the catalyst composition is at or above 580 m$^2$/g. Although a maximum surface area of the catalyst composition has not been determined experimentally, it is believed that an upper limit of 700 m$^2$/g is possible. Obtaining such a high surface area in the range from about 580 to 700 m$^2$/g and using it to isomerize a hydrocarbon feedstock containing dimethylnaphthalenes is the object of one of the embodiments of the subject invention.

The metal that is present in the catalyst composition to supply the hydrogenation-dehydrogenation function is a Group VIII noble metal. The Group VIII noble metals include the metals of the "Platinum Series" and the metals of the "Palladium Series", i.e., platinum, iridium, osmium, palladium, rhodium, and ruthenium. The preferred Group VIII noble metal is platinum. The Group VIII noble metal of the catalytic composition of the present invention will be utilized in an amount from about 0.1 to about 10% by weight of the composition. It is particularly preferred that the metal component be at least about 0.15% by weight and not over 1.0% by weight.

Of course, it is not beyond the scope of the instant invention that the catalyst composition contain a catalytically effective amount of a promoter metal. Examples of such promoter metals include tin, lead, germanium, cobalt, nickel, iron, tungsten, chromium, molybdenum, bismuth, indium, gallium, cadmium, zinc, uranium, copper, silver, gold, tantalum, one or more of the rare earth metals, and mixtures thereof.

Another essential component of the instant invention is the hydrogen form mordenite. While mordenite is naturally occurring, a variety of synthetic mordenites are available commercially, usually in a powder form. These synthetic mordenites can be obtained in both the sodium form and hydrogen form and at varied silica to alumina ratios. It is a preferred embodiment of the present invention that the mordenite be of the hydrogen form and that the silica to alumina ratio be at least 16:1, and more preferably in the range from 16:1 to 60:1. The pretreatment steps taught in the aforementioned references are routinely and typically employed in the manufacture of commercially available mordenite powders which meet the requirements as a starting material as set forth in the present invention. These pretreatment steps are used to increase the silica to alumina ratio of the mordenite zeolite and to convert the sodium form to the more desirable hydrogen form.

The hydrogen form mordenite is incorporated with alumina and formed into a catalytic composite. The formed catalytic composite may be prepared by any known method in the art including the well-known oil drop and extrusion methods. The hydrogen form mordenite may be present in an amount within the range of 50 to about 99.5 wt. %, preferably within the commercially desirable range of 75 to about 95 wt. %. Thus, the alumina is preferably present in an amount within the range of from about 5 to about 25 wt. %, based on total weight of the catalyst composition.

The preferred alumina for use in the present invention is selected from the group consisting of gamma-alumina, eta-alumina, and mixtures thereof. Most preferred is gamma-alumina. Other refractory inorganic oxides which are contemplated include, for example, silica gel, silica-alumina, magnesia-alumina, zirconia alumina, phosphorus-containing alumina, and the like.

Surprisingly and unexpectedly, it has been found that a catalyst composition prepared in accordance with and containing the components as claimed in the invention will possess a surface area higher than any catalyst heretofore described in the art. This high surface area of at least 580 m$^2$/g is surprising when one considers not only the diluting affect of an alumina support material having relatively low surface area (maximum approximately 250 m$^2$/g), but also considering the lowering of surface area caused by the particular forming technique employed. As exemplified herein below, catalyst of the prior art do not obtain the high surface area of the instant catalyst and thus demonstrate inferior performance, particular as isomerization catalyst. The prior art does not teach or suggest how to obtain a mordenite/alumina catalyst having a surface area of at least 580 m$^2$/g. Surface area as referred to herein, is determined by employing the Langmuir method of correlating adsorption/desorption isotherm data. The Langmuir method is especially suitable for catalytic composites containing high percentages of crystalline aluminosilicates. The data needed for the Langmuir method is typically obtained by well known adsorption/desorption apparatuses, preferably a nitrogen adsorption/desorption apparatus. Therefore, the present invention allows for a catalyst composition using a high surface area mordenite without loss of this surface area when formed with alumina to give a commercially acceptable formulation. Likewise, the benefit of the presence of alumina, which imparts, among other things, strength to the catalyst composition, may be achieved without penalty with regard to the surface area of the mordenite.

Any method may be employed which results in a final catalyst composite having at least a surface area of 580 m$^2$/g. Catalyst compositions with high surface areas can be arrived at in a number of ways, such as, using a hydrogen form mordenite powder which inherently has a very high surface area, or by having one component of he composite, which has a high surface area, in great proportion to other components. A preferred method of achieving a surface area of at least 580 m$^2$/g is to contact the formed catalytic composite with an acidic aqueous solution. This acidic aqueous solution may contain ammonium ions. The formed catalyst composite may be dried and/or calcined prior to its contact with aqueous solution.

The acidic nature of the aqueous solution is attained by employing an acid. Particularly suitable are strong mineral acids such as $H_3PO_4$, $H_2SO_4$, $HNO_3$, and HCl. HCl is the preferred acid of the present invention. Of course, it is contemplated that mixtures of various acides may also be employed. If the acidic aqueous solution contains ammonium ions, the preferred source of these ions if $NH_4Cl$, but any ammonium compound which can form ammonium ions, such as $NH_4OH$, $NH_4NO_3$, $NH_4$ sulfates, $NH_4$ phosphates and the like, should be suitable.

Concentrations on the acid and ammonium ions in the aqueous solution are not critical and can vary from 0.5 M to 6 M for the acid concentration and 0.5 M to 4 M for the ammonium ion concentration. Particularly good results are obtained using a solution containing acid and ammonium ion concentrations within the range of 2 to 5 M for the acid and 1 to 3 M for the ammonium ion.

A plurality of methods for contacting the formed catalytic composite and the acidic aqueous solution are envisioned with no one method known to give a particular advantage. Such contacting methods may include, for example, a stationary catalyst bed in a static solution, a stationary catalyst bed in an agitated solution, a stationary catalyst bed in a continuously flowing solution, or any other means which efficiently contacts the catalyst composition with the acidic aqueous solution. The temperature of the contacting solution should be within the range of 25° C. to about 100° C., preferably within the range of from about 50° C. to about 98° C. The time required for the contacting step will depend upon concentrations, temperature and contacting efficiency. In general, the contacting time should be at least 0.5 hour, but not more than 4 hours, preferably between 1 and 3 hours in duration.

As a result of contacting the formed catalytic composite with the acidic aqueous solution, an increase in the measured surface area is observed. Surprisingly and unexpectedly, this increase in surface area, to 580 m$^2$/g or higher, is not accompanied by an increase in the silica to alumina ratio of the hydrogen form crystalline aluminosilicate as measured by Magic Angle Spinning NMR (MASNMR). The MASNMR technique, which is a well known analytical method of the art, indicates no reduction in the framework tetrahedral aluminum atoms of catalyst compositions of the present invention. Although it is not certain the exact reason why the surface area is higher after contacting the formed catalytic composite, it is believed that the acidic aqueous solution is removing occluded ions from the mordenite which are deposited therein as a result of the forming technique employed.

The catalyst of the invention has particular utility for the isomerization of isomerizable hydrocarbons. Included in the group of isomerizable hydrocarbons are saturated hydrocarbons including paraffin hydrocarbons and is still more particularly suitable for the hydro-isomerization of dimethylnaphthalene isomers to produce 2,6-dimethylnaphthalene. The isomerization reaction can be conducted over a wide range of temperatures, but, in general, in the range from about 100° C. to about 500° C. Space velocities from about 0.1 to about 10 liquid volumes per hour of said isomerizable hydrocarbons per volume of said catalytic composite are preferred with reaction zone pressures preferably within the range from about 1 to about 70 atmospheres. It is particularly desirable to carry out the isomerization reaction in the presence of hydrogen preferably in the range from about 0.5 to about 10 moles of $H_2$ per mole of isomerizable hydrocarbon. The function of the hydrogen is primarily to improve catalyst life, apparently by preventing polymerization of intermediate reaction products which would otherwise polymerize and deposit on the catalytic composite. It is not necessary to employ pure hydrogen since hydrogen containing gases, e.g., hydrogen-rich gas from the catalytic reforming of naphthas are suitable.

Preferably, a hydrocarbon containing at least 10 wt. % dimethylnaphthalene isomers is utilized as the feedstock of the instant process. Isomerization reaction zone conditions most suitable for the isomerization of dimethylnaphthalenes into 2,6-dimethylnaphthalenes include a temperature of from 300° to 450° C., a pressue of from 1 to 20 atmospheres, a liquid hourly space velocity of from 0.5 to 5 hr$^{-1}$, and a hydrogen to hydrocarbon molar feed ratio of from 1 to 7.

It is an aspect of this invention that the isomerization process be a complete process. That is to say, the isomerization process will comprise a reaction section and other sections such as gas recycle, liquid recycle, product recovery, and the like such that the process is viable and efficient. Examples of some of the product recovery techniques that could be employed alone or in combination in the product recovery zone of this conversion process are: distillation including vacuum, atmospheric, and superatmospheric distillation; extraction techniques including, for example, liquid/liquid extractions, vapor/liquid extractions, supercritical extractions and other; absorption techniques, and any other known mass transfer techniques which can achieve the recovery of the desired products.

It is anticipated that a most effective permeation of the process of the instant invention would be one in which the isomerization reaction product containing desired 2,6-dimethylnaphthalene isomers undergoes processing to remove the 2,6-DMN isomer therefrom. The remaining product containing all other DMN isomers would then be recycled to the isomerization reaction zone for further processing. This method would maximize the production of 2,6-dimethylnaphthalene from a dimethylnaphthalene-containing feedstock. It is anticipated this type of process would be most effective with a feedstock containing at least 25 wt. % dimethylnaphthalenes.

The following examples are presented for purposes of illustration only and are not intended to limit the scope of the present invention.

EXAMPLE 1

This example describes the method of formulating the catalyst of the instant process. A 9:1 weight ratio mixture of a hydrogen form, low sodium partially dealuminated synthetic mordenite powder (marketed by Union Carbide under the name LZ-M8) and alumina was admixed with an acidified peptization solution and extruded by means known in the art. The extruded composite was dried. The dried extrudate prior to calcining and platinum addition was contacted with an acidic aqueous solution containing ammonium ions. This solution contained 10 wt. % HCl and 10 wt. % $NH_4Cl$. Contacting of the solution and the extrudate was performed at 60° C. for 120 minutes at a solution to zeolite weight ratio of 25:1. The extrudate was subsequently dried, calcined and impregnated with platinum such that the catalyst had a platinum level of 0.3 wt. %. The catalyst had a surface area of 622 m$^2$/g.

EXAMPLE II

The catalyst formulation of Example 1 consisting of platinum supported on a hydrogen form mordenite gamma-alumina composite was evaluated for isomerization performance in a flow reactor processing a hydrocarbon feedstock described in Table 1 below.

TABLE 1

| Feed Analysis | |
|---|---|
| Compound | Wt. % |
| Non-Aromatics | 0.00 |
| Toluene | 0.01 |
| Biphenyl | 1.04 |
| DiHydroNaphthalene | 0.43 |
| Naphthalene | 0.02 |
| 1-MeNaphthalene | 0.11 |
| 2-MeNaphthalene | 0.09 |
| 1-EtNaphthalene | 4.19 |
| 2-EtNaphthalene | 13.26 |
| 1,2+1,8-DiMeNaphthalene | 1.66 |
| 1,3+1,6-DiMeNaphthalene | 36.58 |
| 1,4-DiMeNaphthalene | 2.84 |
| 1,5-DiMeNaphthalene | 2.22 |
| 1,6-DiMeNaphthalene | 0.00 |
| 1,7-DiMeNaphthalene | 14.91 |
| 1,8-DiMeNaphthalene | 0.00 |
| 2,3-DiMeNaphthalene | 4.81 |
| 2,6-DiMeNaphthalene | 1.97 |
| 2,7-DiMeNaphthalene | 15.00 |
| Heavies | 0.86 |
| Total | 100.00 |

The operating conditions used to test the dimethylnaphthalene isomerization performance of the catalyst of this process comprised a reactor pressure of 3.4 atmospheres, a liquid hourly space velocity of 1.0 hr$^{-1}$, an $H_2$ to feed hydrocarbon molar ratio of 5.0, and a temperature of 375° C. Test run data, specifically the amount of 2,6-dimethylnaphthalene isomer, in the reaction product was used as a measure of isomerization performance. The ability of the instant process to produce an isomerization product richer in the 2,6-dimethylnaphthalene isomer than the corresponding feedstock is evidenced by the pilot plant results in Table 2 below.

TABLE 2

| Hours On-Stream | Wt. % 2,6-DMN in Product |
| --- | --- |
| 2 | 9.8 |
| 3 | 9.9 |
| 4 | 9.9 |
| 5 | 9.9 |

The feed to the process in this case contained 1.97 wt. % of the 2,6-DMN isomer while the product contained almost 10 wt. % of the same isomer. It is evident from this result that the isomerization process of this invention is able to produce a product rich in the desired 2,6-dimethylnaphthalene isomer. The composition of the entire reactor effluent stream after 5 hours on stream can be found in Table 3 below.

TABLE 3

| Product Analysis (5 Hrs. On-Stream) | |
| --- | --- |
| Compound | Wt. % |
| Non-Aromatics | 0.76 |
| Toluene | 0.47 |
| Biphenyl | 0.56 |
| DiHydroNaphthalene | 4.70 |
| Naphthalene | 0.96 |
| 1-MeNaphthalene | 0.47 |
| 2-MeNaphthalene | 1.27 |
| 1-EtNaphthalene | 2.93 |
| 2-EtNaphthalene | 10.98 |
| 1,2+1,8-DiMeNaphthalene | 2.59 |
| 1,3+1,6-DiMeNaphthalene | 24.62 |
| 1,4-DiMeNaphthalene | 2.82 |
| 1,5-DiMeNaphthalene | 1.68 |
| 1,6-DiMeNaphthalene | 0.00 |
| 1,7-DiMeNaphthalene | 12.07 |
| 1,8-DiMeNaphthalene | 0.00 |
| 2,3-DiMeNaphthalene | 6.49 |
| 2,6-DiMeNaphthalene | 9.95 |
| 2,7-DiMeNaphthalene | 13.40 |
| Heavies | 3.28 |
| Total | 100.00 |

What is claimed is:

1. A process for the isomerization of dimethylnapthalenes in a hydrocarbon feedstock to provide a concentration of a dimethylnaphthalene isomer in the isomerization reaction product which is greater than that of the concentration of the same dimethylnaphthalene in the hydrocarbon feedstock, wherein the process comprises contacting the hydrocarbon feedstock with an isomerization catalyst in an isomerization reaction zone operating at isomerization reaction conditions and recovering the isomerization reaction zone products where the isomerization catalyst comprises a Group VIII metal, a hydrogen form mordenite dispersed in an alumina matrix, said catalyst comprising from about 5 to 25 percent by weight of alumina, and wherein the support is contacted with an acidic aqueous solution after it is formed, said contacting occurring at conditions selected to increase the surface area of the composite to at least 580 m$^2$/g without increasing the silica to alumina ratio of the mordenite.

2. The process of claim 1 wherein said isomerization catalyst is spherical, cylindrical, and/or granular in shape.

3. The process of claim 1 wherein the alumina is selected from the group consisting of gamma-alumina, eta-alumina, and mixtures thereof.

4. The process of claim 3 wherein the alumina is gamma-alumina.

5. The process of claim 1 wherein the hydrogen form mordenite has a silica to alumina ratio of at least 16:1.

6. The process of claim 1 wherein the Group VIII metal component is platinum or palladium.

7. A process for the isomerization of a hydrocarbon feedstock containing dimethylnaphthalenes such that the concentration of the 2,7- or 2,6-dimethylnaphthalene isomer in the isomerization reaction product is greater than the concentration of the 2,7- or 2,6-dimethylnaphthalene in the hydrocarbon feedstock wherein the process comprises contacting the hydrocarbon feedstock with an isomerization catalyst in an isomerization reaction zone operating at isomerization reaction conditions including a temperature in the range of from 100° C. to 500° C., a pressure of from about 1 to 70 atmospheres, a liquid hourly space velocity of from about 0.1 to 10 hr$^{-1}$, and a hydrogen to hydrocarbon molar feed ratio of from about 0.5 to 10, and recovering the isomerization reaction zone products where the isomerization catalyst support comprises a hydrogen form mordenite dispersed in a gamma-alumina matrix and platinum, said catalyst comprising from about 5 to 25 percent by weight gamma-alumina and wherein the support is contacted with an acidic aqueous solution after it is formed, said contacting occurring at conditions selected to increase the surface area of the composite to at least 580 m$^2$/g without increasing the silica to alumina ratio of the mordenite.

8. The process of claim 7 further characterized in that the platinum is present in the isomerization catalyst in an amount ranging from 0.15 to 1.0 wt. %.

9. The process of claim 7 further characterized in that the hydrocarbon feedstock contains 10 wt. % or more of dimethylnaphthalenes.

10. A process for the isomerization of a hydrocarbon feedstock containing at least 25 wt. % dimethylnaphthalenes such that the concentration of the 2,6-dimethylnaphthalene isomer in the isomerization reaction product is greater than the concentration of the 2,6-dimethylnaphthalene isomer in the hydrocarbon feedstock which process comprises contacting the hydrocarbon feedstock with an isomerization catalyst in an isomerization reaction zone operating at isomerization reaction conditions including a temperature of from 300° to 450° C., a pressure of from about 1 to 20 atmospheres, a liquid hourly space velocity of from about 0.5 to 5 hr$^{-1}$, and a hydrogen to hydrocarbon molar feed ratio of from about 1 to 7, and recovering the isomerization reaction zone products where the isomerization catalyst comprises from 0.15 to 1.0 wt. % platinum, and a support comprising a hydrogen form mordenite dispersed in a gamma-alumina matrix, and support containing from about 5 to 25 wt. % gamma-alumina, and wherein the support is contacted with an acidic aqueous solution after it is formed, said contacting occurring at conditions selected to increase the surface area of the composite to at least 580 m$^2$/g without increasing the silica to alumina ratio of the mordenite.

* * * * *